(12) United States Patent
Kudo

(10) Patent No.: US 8,460,272 B2
(45) Date of Patent: Jun. 11, 2013

(54) METHOD AND APPARATUS FOR EXTENSIBLE INTRAVENOUS DRIP LINE

(76) Inventor: Susan Leeds Kudo, Pacific Palisades, CA (US)

( * ) Notice: Subject to any disclaimer, the term of this patent is extended or adjusted under 35 U.S.C. 154(b) by 752 days.

(21) Appl. No.: 12/454,808

(22) Filed: May 22, 2009

(65) Prior Publication Data

US 2010/0298813 A1    Nov. 25, 2010

(51) Int. Cl.
*A61M 25/02* (2006.01)
*A61M 25/00* (2006.01)
*A61M 5/31* (2006.01)

(52) U.S. Cl.
USPC .............................. 604/524; 604/179; 604/239

(58) Field of Classification Search
USPC .................. 604/524, 179, 239; 242/570, 588, 242/588.2; 138/125, 129, 119, 107
See application file for complete search history.

(56) References Cited

U.S. PATENT DOCUMENTS

| | | | | |
|---|---|---|---|---|
| 4,088,136 A | * | 5/1978 | Hasslinger et al. | 604/179 |
| 4,292,969 A | * | 10/1981 | Raible et al. | 604/250 |
| 4,569,348 A | * | 2/1986 | Hasslinger | 604/179 |
| 4,666,434 A | * | 5/1987 | Kaufman | 604/179 |
| 4,699,613 A | * | 10/1987 | Donawick et al. | 604/80 |
| 5,163,923 A | * | 11/1992 | Donawick et al. | 604/257 |
| 5,728,053 A | * | 3/1998 | Calvert | 602/5 |
| 5,776,105 A | * | 7/1998 | Corn | 604/174 |
| 6,053,170 A | * | 4/2000 | Padilla, Jr. | 128/877 |
| 6,247,211 B1 | * | 6/2001 | Bell | 24/306 |
| 6,874,500 B2 | * | 4/2005 | Fukunaga et al. | 128/204.18 |
| 6,879,853 B2 | * | 4/2005 | Meaney et al. | 600/420 |
| 6,910,505 B2 | * | 6/2005 | Weck et al. | 138/109 |
| 2008/0071224 A1 | * | 3/2008 | Forsyth | 604/179 |

* cited by examiner

*Primary Examiner* — Kevin C Sirmons
*Assistant Examiner* — Michael J Anderson
(74) *Attorney, Agent, or Firm* — A. N. Seidman

(57) ABSTRACT

The extensible intravenous ("i.v.") drip line tubing uses a helical accordion support structure on which the i.v. tubing is attached. The helical accordion backbone has some tendency to spring back, but this is not relied upon to extend and return the i.v. tubing it carries. The carrier structure keeps the i.v. tubing from getting tangle or kinked. A centrally located retractable line, which is located within the center of the helical accordion structure, acts as the retracting mechanism, as it tends to allow the accordion structure to be pulled into an extended position, while upon rewinding the central cord, the helical accordion support structure can be pushed toward a collapsed position without the i.v. drip line tubing becoming tanked, kinked, and thereby blocked. As a safety feature, so the i.v. line does not encounter and strain between it and the point of entry of the i.v. line into the patient, is one or more wrist and or armbands to which the i.v. carrier is attached by a short, strong line.

17 Claims, 15 Drawing Sheets

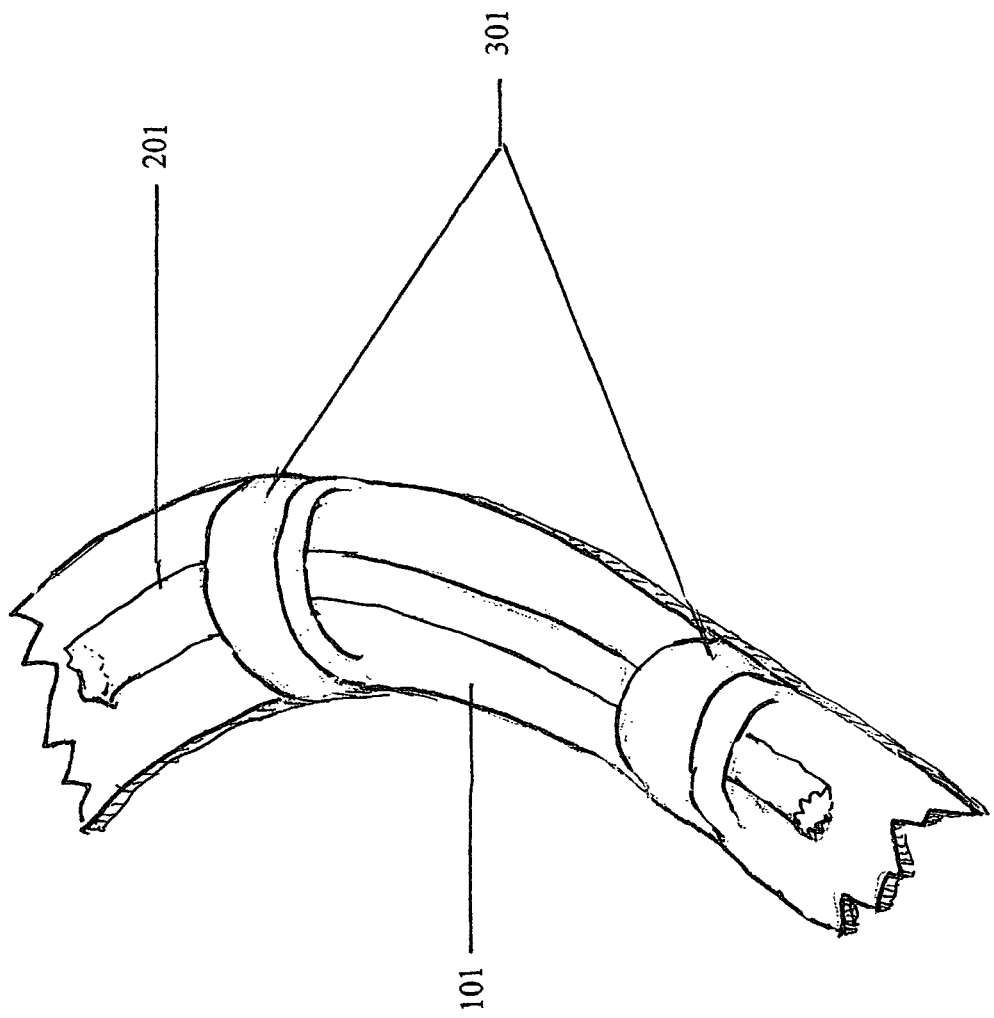

METHOD AND APPARATUS FOR EXTENSIBLE INTRAVENOUS DRIP LINE

FIELD OF THE INVENTION

The invention relates to intravenous drip lines which can extend and retract over a distance of many tens of feet.

BACKGROUND OF THE INVENTION

Medical patients are often placed on an intravenous (i.v.) drip line. Typically this i.v. line is fed from a source such as a 1 liter bag of some per-cent saline or some percent glucose. Typically the line has junction points and insertion points. The junction points allow one i.v. drip line to attach to another line. An insertion points, sometimes combined with one or more junction points, allows for the injection into the line of medication, typically by a syringe adapted to be inserted temporarily into the insertion point.

One goal which doesn't appear to be satisfactorily solved is to make the i.v. drip line extensible so that a patient, for example, is able to get out of bed, while attached to the i.v. drip line and traverse a distance to a bathroom and then return to bed, without having to roll along an i.v. source ("bag") holder. The bag holder is typically a relatively large and heavy object extending upward and on rollers or wheels. If the patient currently needs to move around, the patient must move the i.v. bag holder along with him or her. This tends to be awkward, especially for a quick trip to the bathroom.

An ideal approach to solving this problem would to have an extensible i.v. tube that could extend and return to its place of origin. This ideal approach would use existing i.v. tubing and such junction points and insertion points which already exist, are approved for medical use by the Food and Drug Administration.

One difficulty can be noted up front: the i.v. tubing is very flexible and relatively of small diameter and relatively thin walled. This difficulty may preclude some direct approaches to answering the question of how to translate the desired result into a workable apparatus.

It is of interest to review prior art. In this conjunction it is noted that at least in one's typical experience in a modern hospital, no such extensible i.v. lines have been encountered. This is based on the inventor's anecdotal experiences.

SUMMARY OF THE INVENTION

This mechanical composition invention fulfills a long felt need. Although a number of inventors have turned their hands to proving a solution to the problem outlined in the "Background of the Invention" section above, and no doubt many Medical Doctors and scientists, engineers and inventors have been subject to hospitalization or observations of those hospitalized, the invention herein, if it were obvious, would have already been invented. Therefore, hindsight alone would not be enough to render this invention obvious.

The invention herein uses a helical accordion support structure ("backbone") backbone on which the i.v. tubing is attached or held. The helical accordion backbone has some tendency to spring back, but this is not relied upon to extend and return the i.v. tubing it carries. The carrier structures keeps the i.v. tubing from getting tangle or kinked.

Instead a centrally located line retractable line, which is located within the center of the helical accordion structure, acts as the retracting mechanism, as it tends to allow the accordion structure to be pulled into an extended position, while upon rewinding the central cord, the helical accordion support structure.

An additional feature to help insure safety, so the i.v. line does not encounter and strain between it and the point of entry of the i.v. line into the patient, is one or more wrist and or armbands to which the i.v. carrier is attached by a short, strong, typically fabric, line The wrist/armband typically uses a Velcro closure, or as will be a double Velcro closure.

This method and apparatus may be used also for patient oxygen lines and for gastro-intestinal tubing, although not necessarily limited to these uses.

BRIEF DESCRIPTION OF THE DRAWINGS

For a more complete understanding of the present invention, and the advantages thereof, reference is now made to the following descriptions taken in conjunction with the accompanying drawings, in which:

FIG. 3a shows one method of attaching i.v. drip line to the accordion carrying structure with closed arches;

DETAILED DESCRIPTION OF THE BEST MODE OF THE INVENTION

The following description is of the best mode presently contemplated for carrying out the invention. This description is not to be taken in a limiting sense, but is merely made for the purpose of describing the general principles of the invention.

Figure 1:
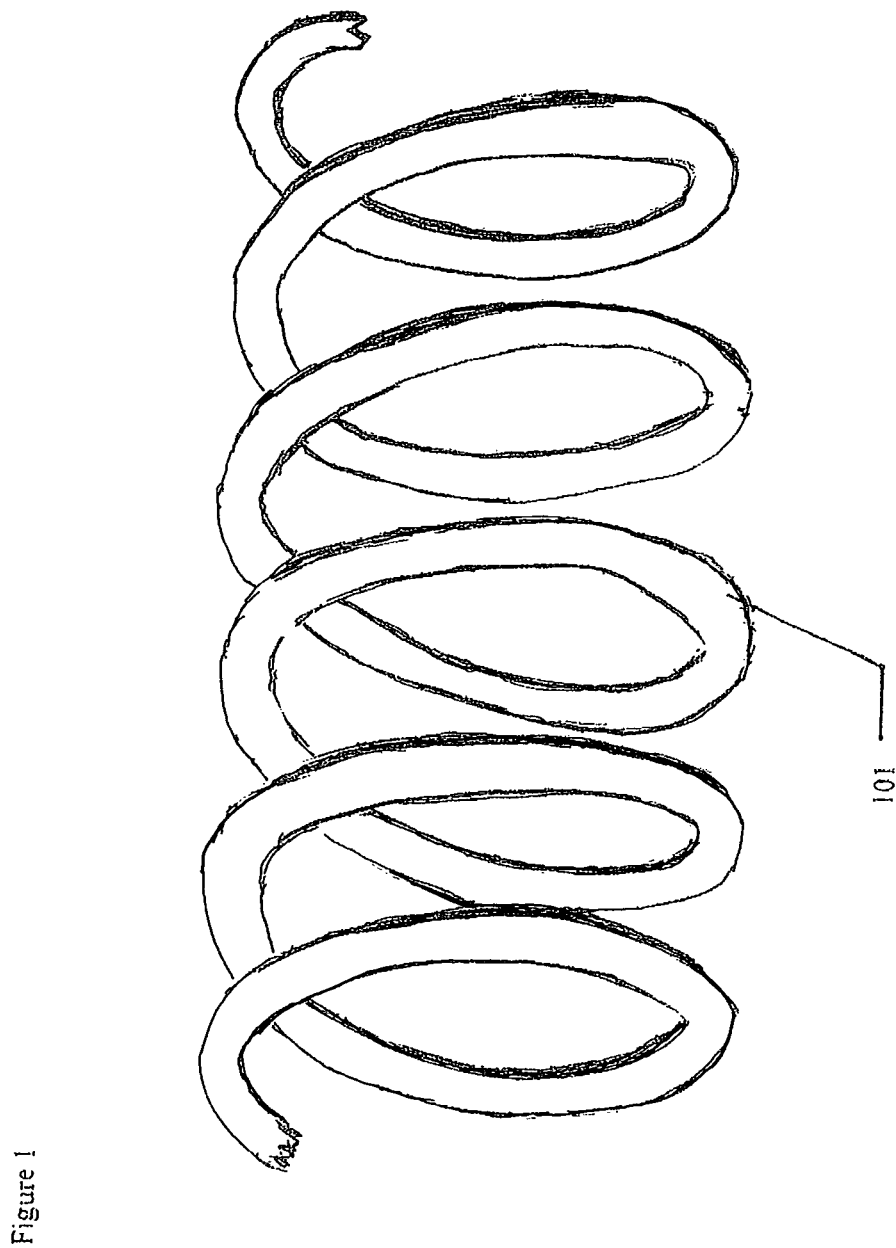
FIG. 1 shows a helical accordion carrying structure.

FIG. 1 shows a helical accordion carrying structure. The purpose of the helical accordion is to provide a support for an intravenous (i.v.) drip line of the type used to deliver, for example, saline or glucose solution, to a patient from a source, typically a 1 liter plastic bag, suspended from an i.v. stand as typically found in a hospital patient's room. One aspect to maintaining a usefully operational i.v. drip line is to keep it from kinking-up and acquiring a kink which blocks fluid from flowing through the kink.

FIG. 1 shows the helical accordion support structure 101. It resembles a a toy sold under a trademark name of "Slinky", U.S. Pat. No. 2,415,012, 1947 issued to R. T. James. Prototypes of this invention were made with a commercially bought metal "Slinky." Two different diameter plastic versions were also used. The purpose of the helical accordion support structure is to keep the i.v. drip line from tangling.

Figure 2:
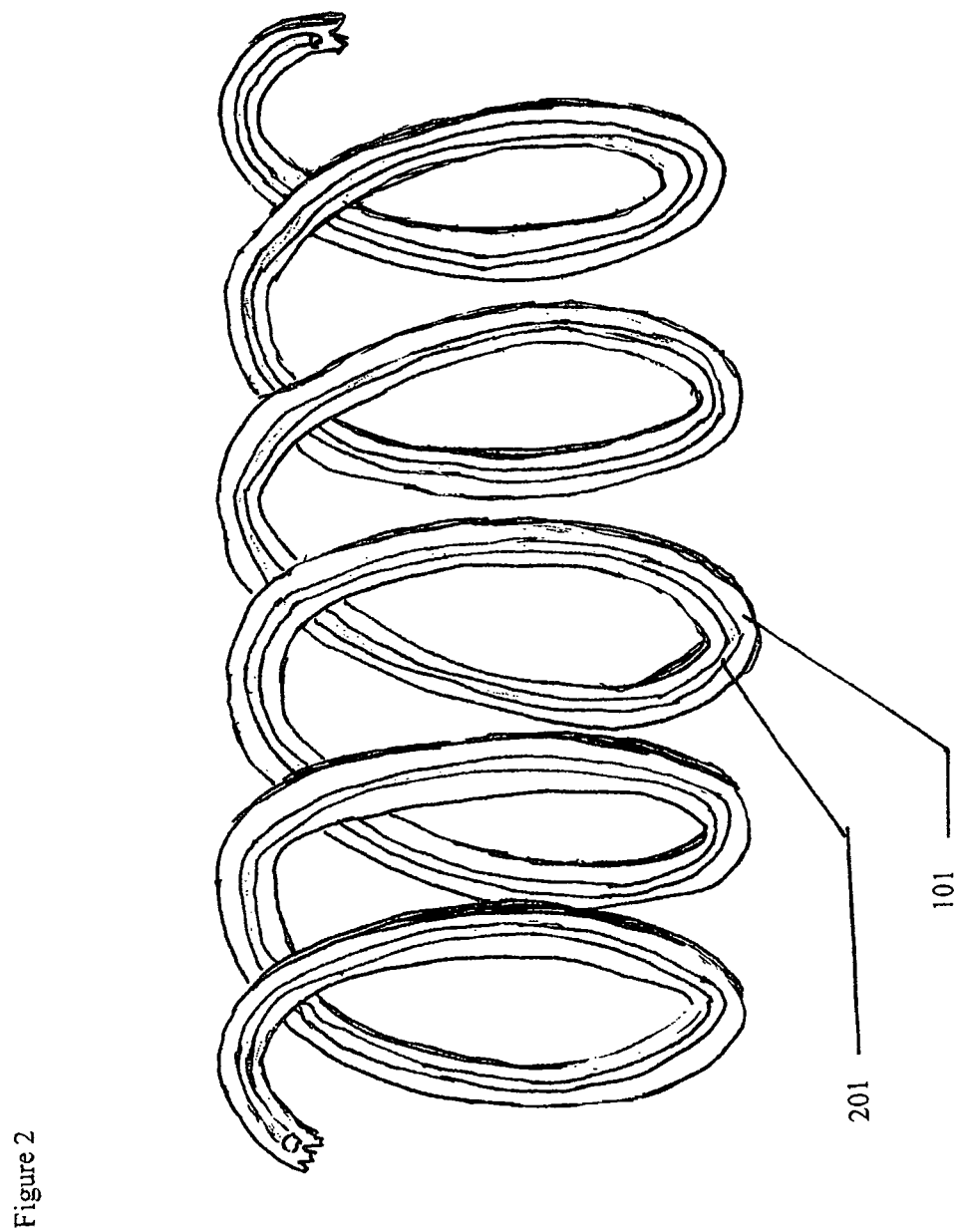
FIG. 2 shows a helical accordion carrying structure with an intravenous drip line in place.

FIG. 2 shows the i.v. drip line 201 in relationship to the helical support structure. It is very important that the i.v. drip line does not become twisted and kinked up. Otherwise the i.v. drip line would not be able to have fluid to continuous drip through it because of the blockage.

The helical accordion support structure 101 provides an indexing topological base such that the sequential ordering of the i.v. drip line 201 is maintained: a first point remains ordered behind a second point in a linear ordering of the i.v. drip line.

Figure 3B:
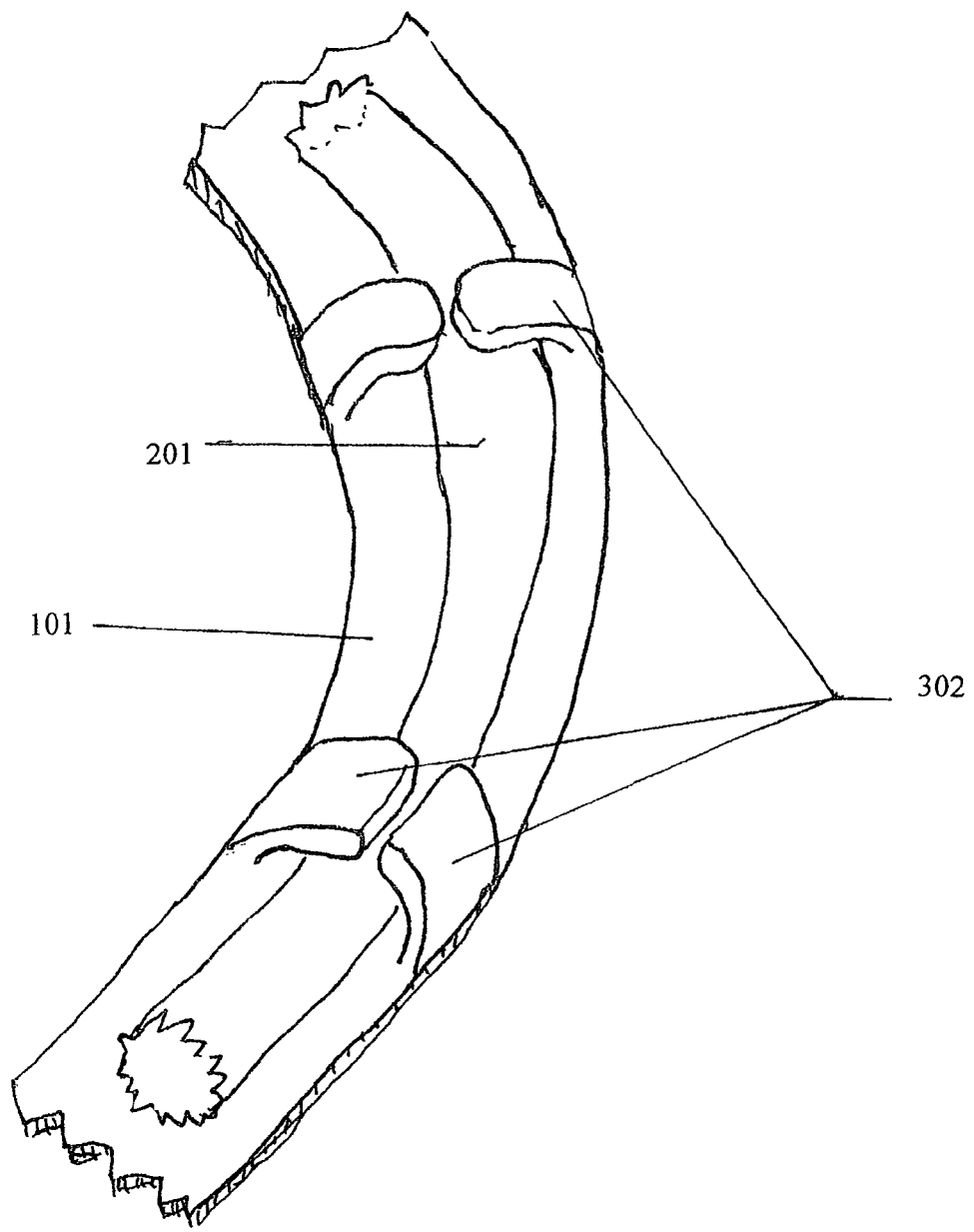
FIG. 3b shows a second method of attaching i.v. drip line to the accordion carrying structure with open arches.

The accordion support structure is necessary but not sufficient to have the extensible i.v. drip line apparatus operate. Before coming to the next component, however, FIGS. 3a-3f show various methods of attaching the i.v. drip line 201 to the helical accordion support structure 101. These methods are meant to be illustrative and not limiting. FIG. 3a shows a flat helical accordion structure with small arches 301 molded into the flat helical structure. The advantage of the flatness of the helical structure 101 is that it maintains a sufficient stiffness against bending.

With the molded arches 301 (FIG. 3a), the i.v. tubing 201 is threaded though the arches 301 and carried around the entire length of the helical accordion support structure 201 as shown in FIG. 2, without the molded in arches 301 being shown).

In another variation of the molded arches 301 of FIG. 3a, FIG. 3b shows molded-in arches 302 with a slight space 303 between the apogees (or "keystone") 304 of the arches 302 meeting. This type of molded-in arch 302 may provide a slightly different method of inserting the i.v. tubing 201. The tubing 201 may just be pushed into the space 303 with an appropriate manufacturing device which may spread the arch apogees 304 slightly so as to facilitate i.v. tubing 201 insertion into the arches 302

Figure 3C:
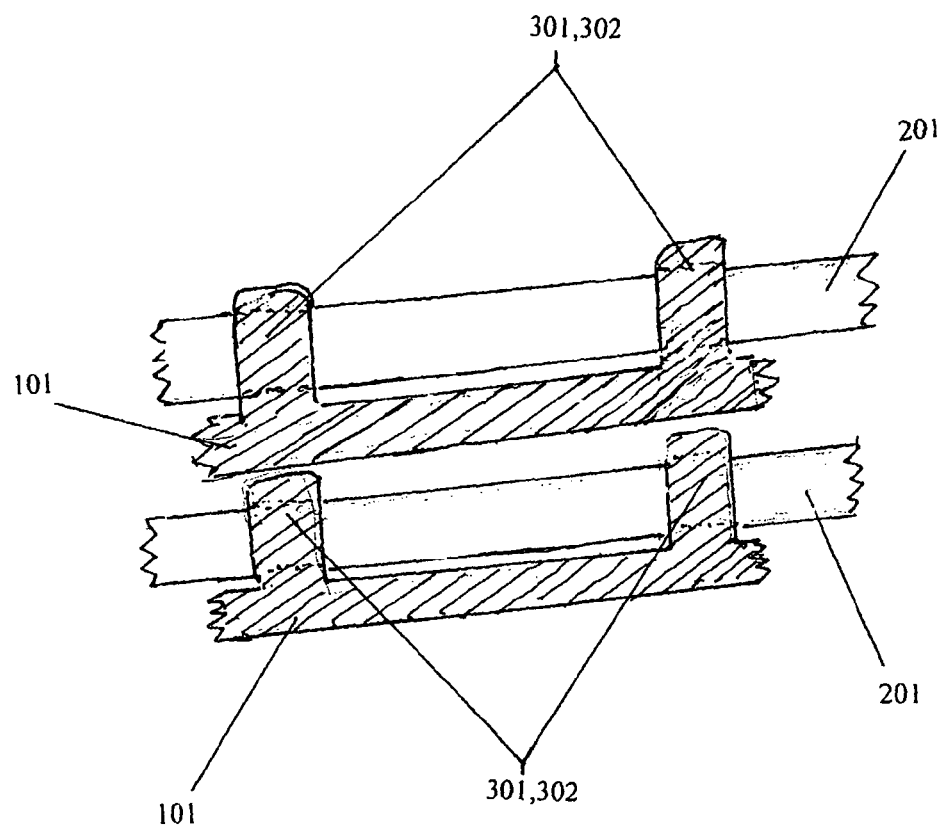
FIG. 3c shows a the protective tendency of the open or closed arches, tending to protect the i.v. drip line from compression.

As shown in FIG. 3c, both these types of arches 310, 302 advantageously act to protect the i.v. drip tubing 201 from any compression from an back of an adjacent "circle" 306 of the helical accordion support structure 101, which is adjacent to the upper surface (upper, as shown in FIG. 3c) "circle" 305 carrying the i.v. drip tubing 201.

Figure 3D:
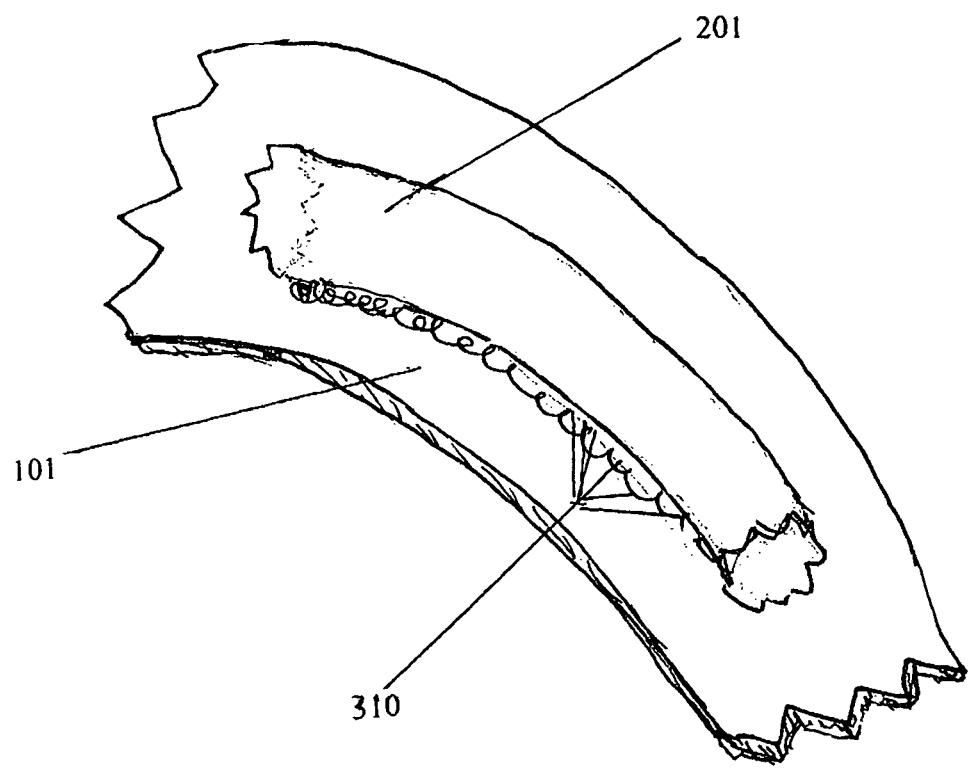
FIG. 3d shows a third method of attaching i.v. drip line to the accordion carrying structure with glue.

FIG. 3d shows the i.v. drip tubing 201 attached to the helical accordion support structure 101 by "glue" 310. The glue 310 needs to be compatible with the i.v. drip tubing 201 so as not to result in penetration and contamination of the i.v. drip tubing 201 by the glue 310. The glue 310 also must not cause structural degradation of the helical accordion support structure 101.

Figure 3E:
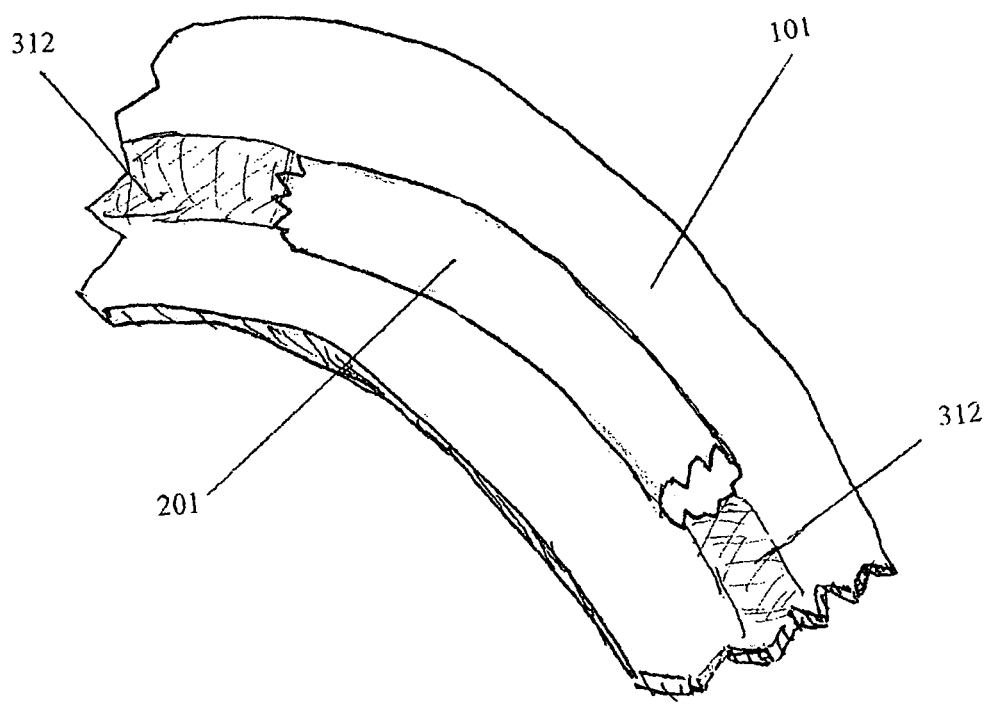
FIG. 3e shows a fourth method of attaching i.v. drip line to the accordion carrying structure with heat welding.

FIG. 3e shows the i.v. drip tubing 201 attached to the helical accordion support structure 101 by "adhesive tape" 311. The adhesive of the tape 311 needs to be compatible with the i.v. drip tubing 201 so as not to result in penetration and contamination of the i.v. drip tubing 201 by the tape 31. The tape also must not cause structural degradation of the helical accordion support structure 101.

Figure 3F:
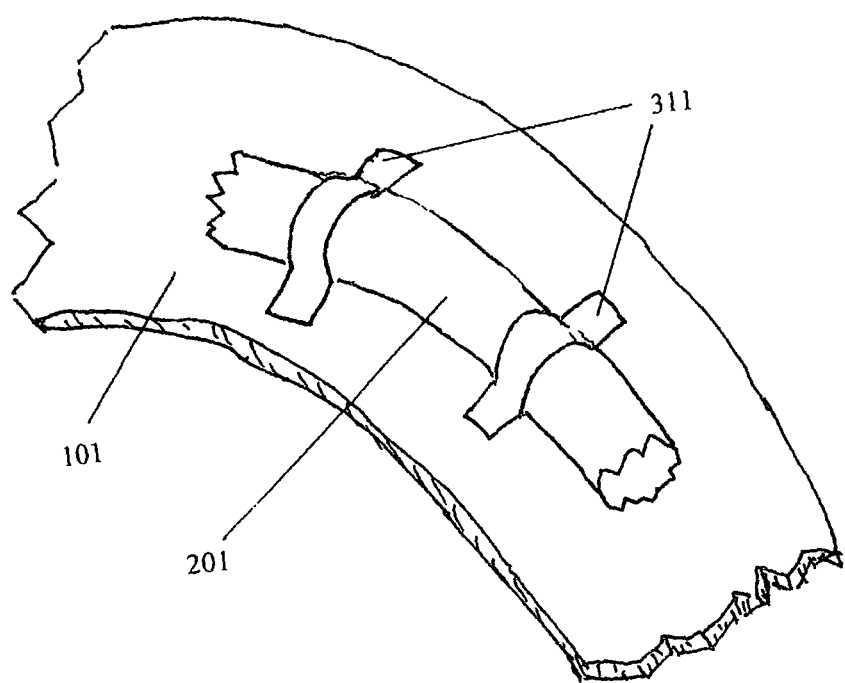
FIG. 3f shows a fifth method of attaching i.v. drip line to the accordion carrying structure with tape.

FIG. 3f shows the i.v. drip tubing 201 attached to the helical accordion support structure 101 by a thermoplastic heat welding method. In this thermoplastic heat welding method, a strip of thermoplastic material 312 is attached to the center of one side of the helical accordion support structure 10 and heat s applied to the thermoplastic material 312 and to the i.v. drip tubing 201. The thermoplastic material 312 may be of the same type plastic as the i.v. drip line 201.

Figure 4:
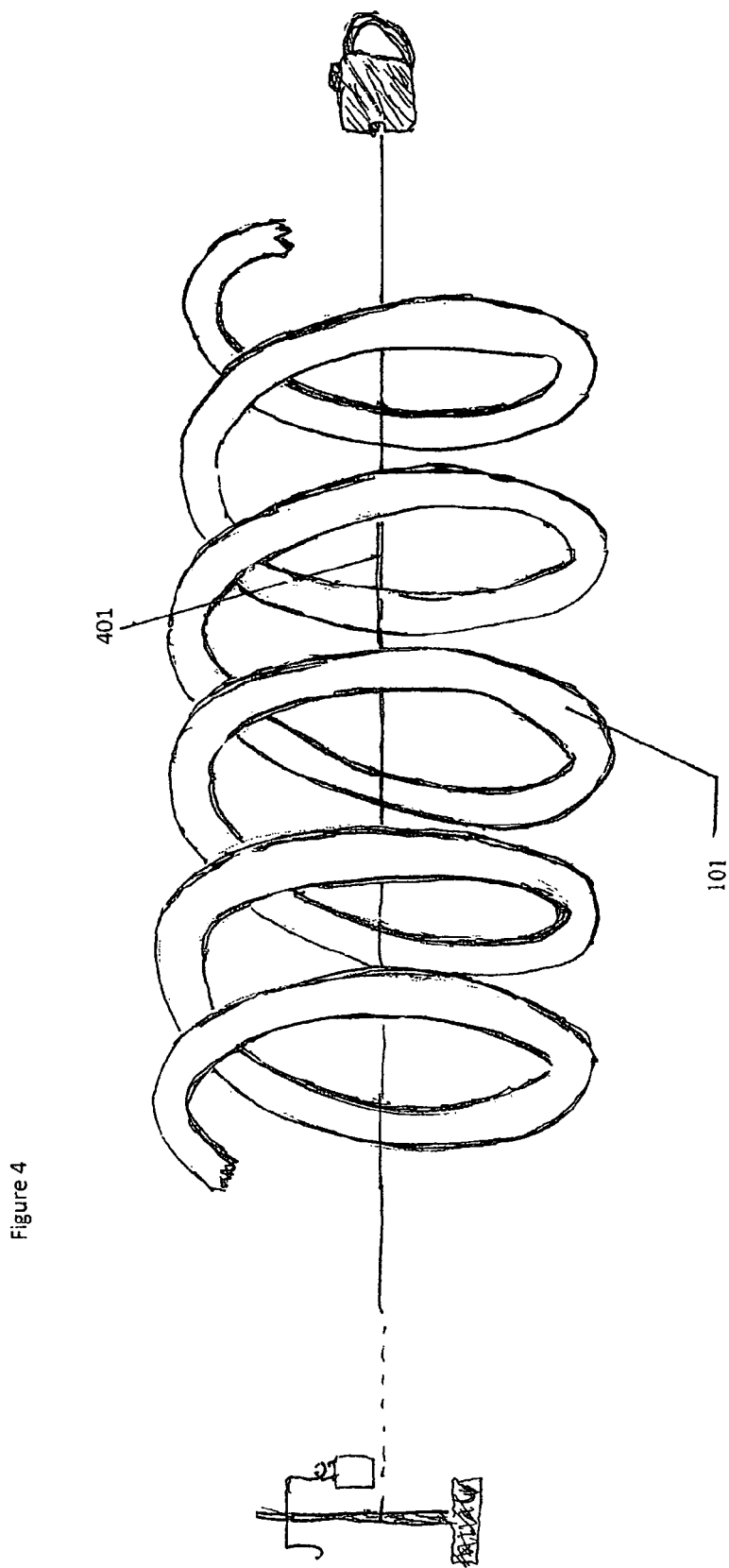
FIG. 4 shows the central retractable line located through the center of the helical accordion support structure.

FIG. 4 shows a "central line" 401 through the center of the helical accordion support structure 101. The term "central line" 401 is used as specifically shown in these figures and is not another i.v. drip line. This central line 401 serves as a support for the helical accordion support structure 101. It also serves to allow the helical accordion support structure 101 to be pulled open and to be pulled shut. The springiness of the accordion aspect of the helical accordion support structure 101 is fairly weak. Also the helical accordion support structure 101 tends to sag even without supporting any i.v. drip line 201. The central control line 401 tends to counteract this sag.

Figure 5:
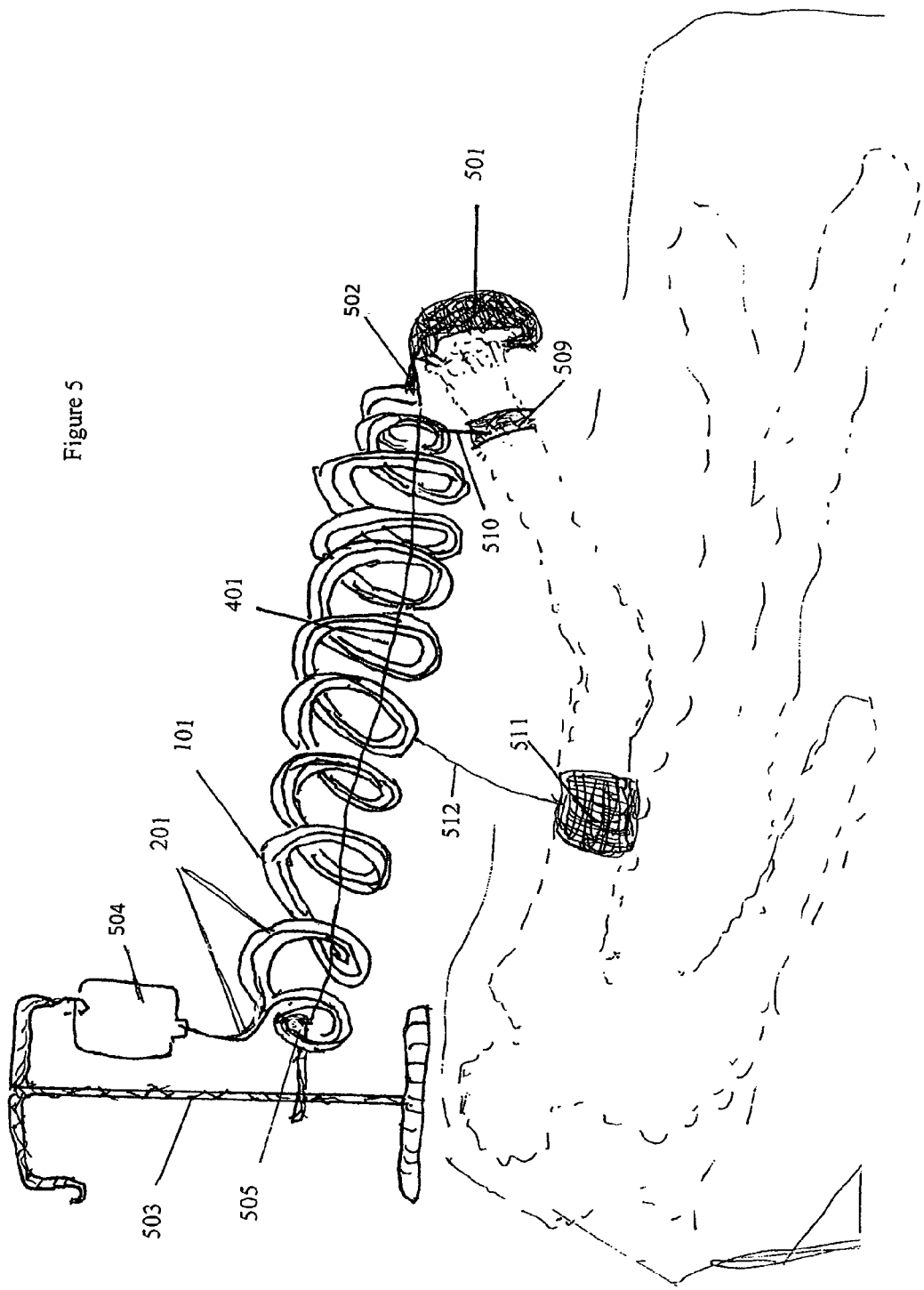
FIG. 5 shows a wristband and armband safety element in place and no part of the living person indicated by dotted lines is part of the invention.

The springiness of the accordion aspect of the helical accordion support structure 101 is easily pulled apart and easily aided in compression by attaching the end 502 of the helical accordion support structure 101, which may be closest to the insertion point of the i.v. line into an arm or wrist vein, to an control element 501 (See FIG. 5).

As shown in FIG. 5, the other end of the central line 401 is anchored to an anchor point 505 of an i.v. stand 503, which may be in the vicinity of the i.v. fluid supply bag 504. The i.v. stand 503 may need an auxiliary bracket attached to it. The central line 401 and the control element 501 are comparable to a commercially available variable length "dog leash," known in the arts, such as one trademarked "flexi", model classic 1. These commercially available adjustable dog leashes essentially can rewind the dog leash line, but don't "haul the dog in," because the rewind spring of this control element 501 is not super-strong. The control element may be based on the adjustable dog leash described here, which also has a thumb trigger for allowing the line, corresponding to the central line 401 to rewind. Any similar mechanism is suitable for the control element 501, even if it is repackaged.

By allowing the control element 501 to pay out line length, a person can walk forward and the accordion aspect of the helical accordion support structure 101 will open up, carrying with it the i.v. drip line 201. Thus the i.v. drip line 201 extends out carried by the accordion structure of helical accordion support structure 101. As the person walks back toward the i.v. drip stand and allows control element 501 to allow the central line to retract, the accordion aspect of the helical accordion support structure 101 tend to close up, contracting with the i.v. drip line 201 attached to it.

The retraction ability of central line 401 rewinding into the control element 501 is fairly weak, but combined with the slight compression ability of the accordion aspect of the helical accordion support structure 101, the helical accordion support structure 101 with the attached i.v. drip line 201 are easily pushed backed to a compressed situation where the total length of the helical accordion support structure 101 is shortened to an fully compressed condition. Similarly, the helical accordion support structure 101 and the attached i.v. drip line are easily extensible by releasing the central line 401 by causing the control element to release and pulling on the control element which is attached to one end of the helical accordion support structure 101.

FIG. 5 also shows two variations of a safety element, a "Velcro" wristband 509 may attach, by a short line 510, to the end of the helical accordion support structure 101. In case the patient drops the control element 501, the wristband 509 will prevent any significant adverse strain being placed on the i.v. drip line where it is inserted into the patient's vein.

Similarly, depending upon the location of the vein insertion point, a similar Velcro armband 511 with a short line 512 may be attached to a patient's arm and a location on the helical accordion support structure 101.

Figure 6A:
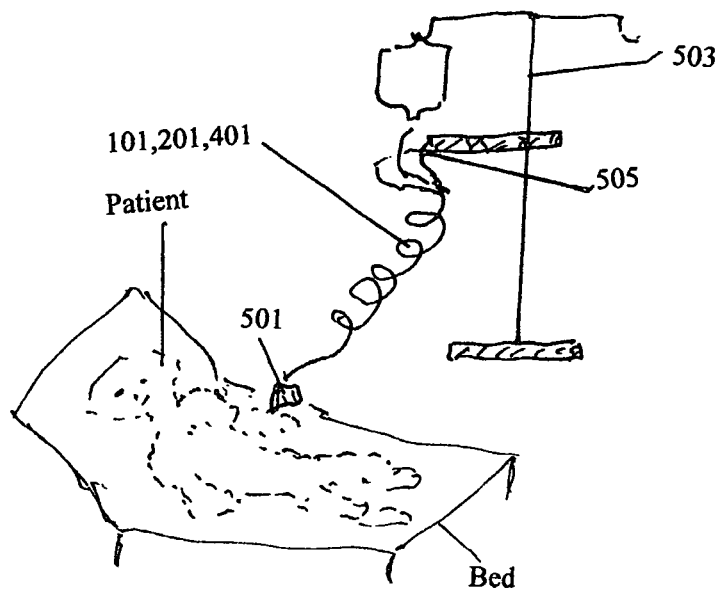
FIG. 6a shows the patient "in bed" with the i.v. extensible system in a collapsed mode.
Figure 6B:
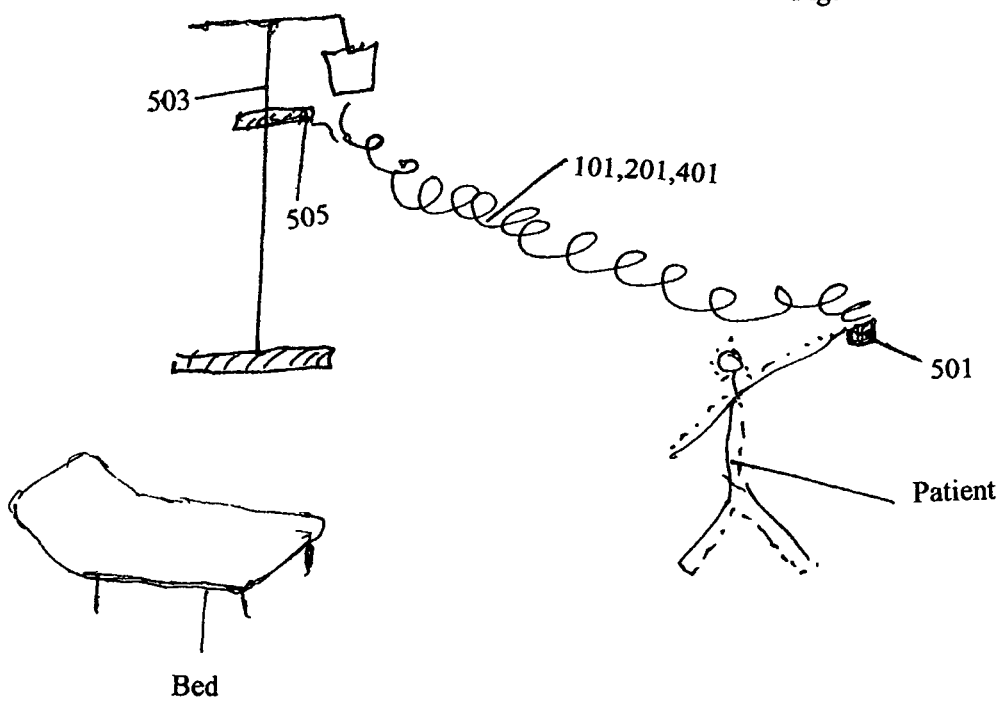
FIG. 6b shows the patient with the i.v. extensible system in an extended position.

These two situations are illustrated in FIGS. 6a and 6b. In FIG. 6a the patient is in bed and the helical accordion support structure 101/i.v. line 201/central line 401 is in the compressed, shortened state. FIG. 6B illustrates the patient out of bed and the helical accordion support structure 101/i.v. line 201/central line is in a more extended position.

Figure 7A:
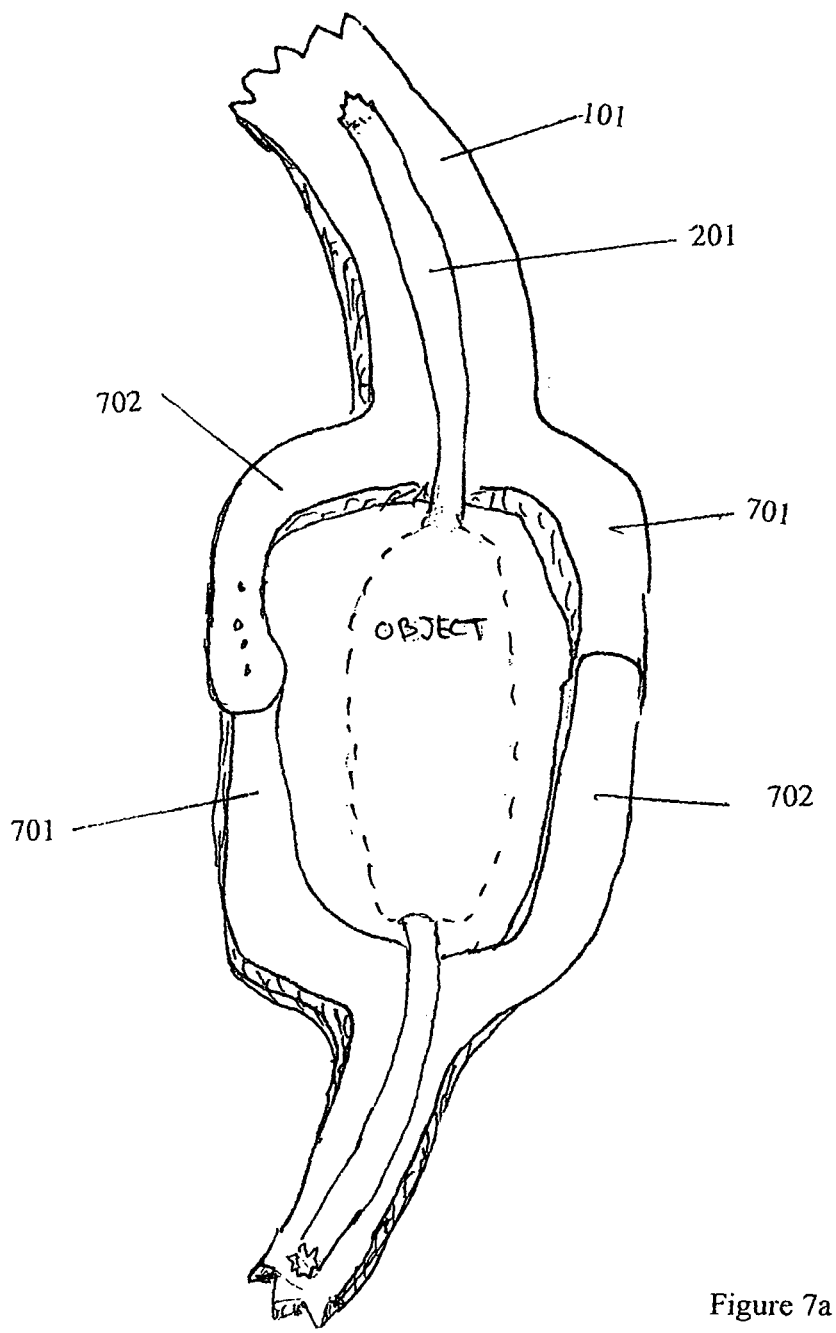
FIG. 7a shows one of many possible systems for integrating the invention with other existing i.v. drip line joint elements and existing i.v. drip line injection elements, with bifurcation into male and female blades.

In order to incorporate current drip line 201 devices (dotted "object" in FIG. 7a), which "object" may be an "object" which serves as connection or junction element to allow two separate i.v. line to join together in a medically satisfactory manner; or it may be an "object," which allows for a location in the i.v. line for the insertion of medication, typically by a hypodermic syringe. FIG. 7a shows such a method/structure for connecting an "object" of this type into the helical accordion support structure 101.

Figure 7B:
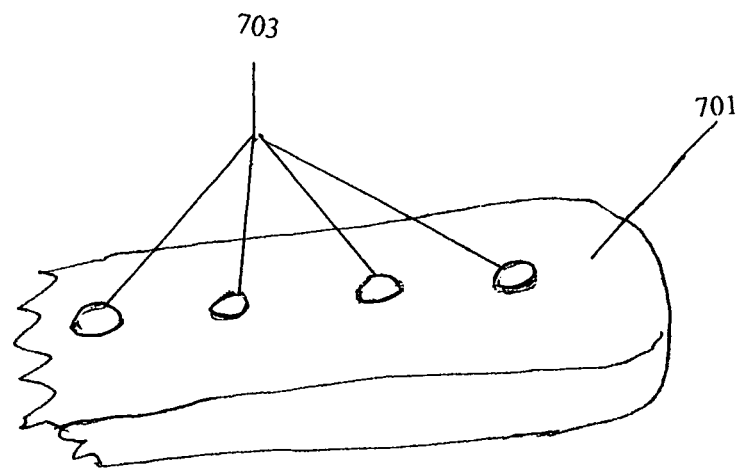
FIG. 7b shows a male blade with raised bumps.
Figure 7C:
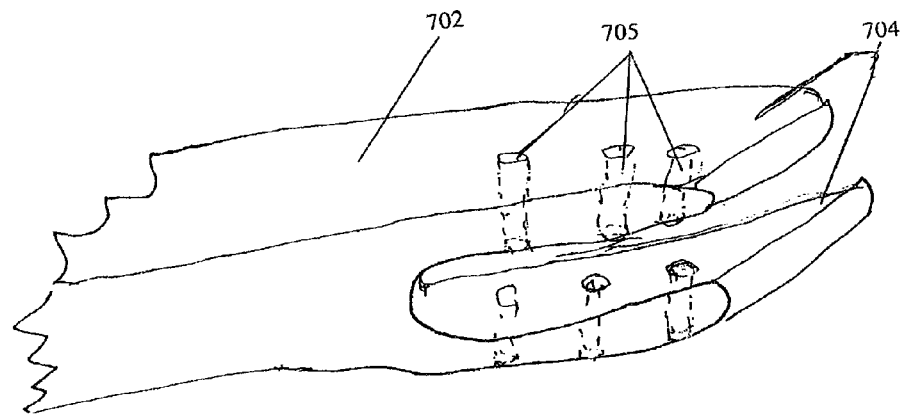
FIG. 7c shows a female doubled blade with receptor holes.

FIG. 7a shows a bifurcation of the helical accordion support structure 101. The helical accordion support structure 101 branched out into two wings 701, 702. The wings come in male/female pairs. FIG. 7b shows the male 701 of the wing pair is a single blade with one or more rounded protrusions 703 on it. FIG. 7c shows the female 702 of the wing pair is a doubled blade 704 with one or more holes 705 in the each blade made so as to accept the protrusions 703 of the male blade 701 as it is pushed between the two blades 704 of the female wing 702 with their corresponding receiving holes 705.

Figure 7D:
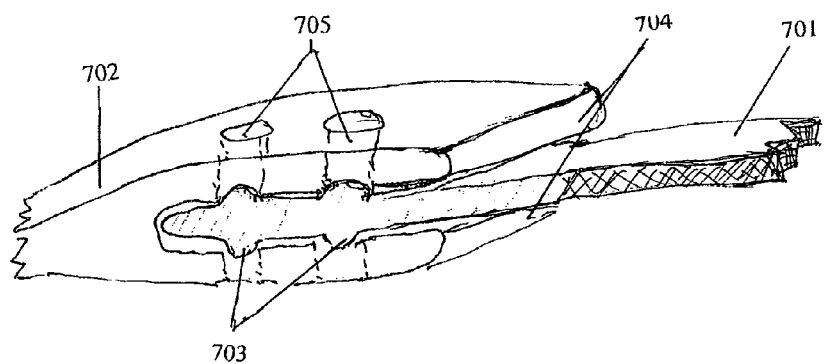
FIG. 7d mated male and female blade.

FIG. 7d shows the mated blade of the male blade 701 with the mated female double 704 blade 702. It shows the protrusions or bumps 703 on the male blade 701 seated in the holes 705 of the female blade 702 in its doubled configuration 704.

Smallest diameter compatible with radius of curvature of i.v. drip line 201 is best because the extra length is $2\pi r$, which compared with the spacing (about h=o.d. of i.v. drip tubing. But one wants also to keep ease of expansion.

Figures 8A, 8B:
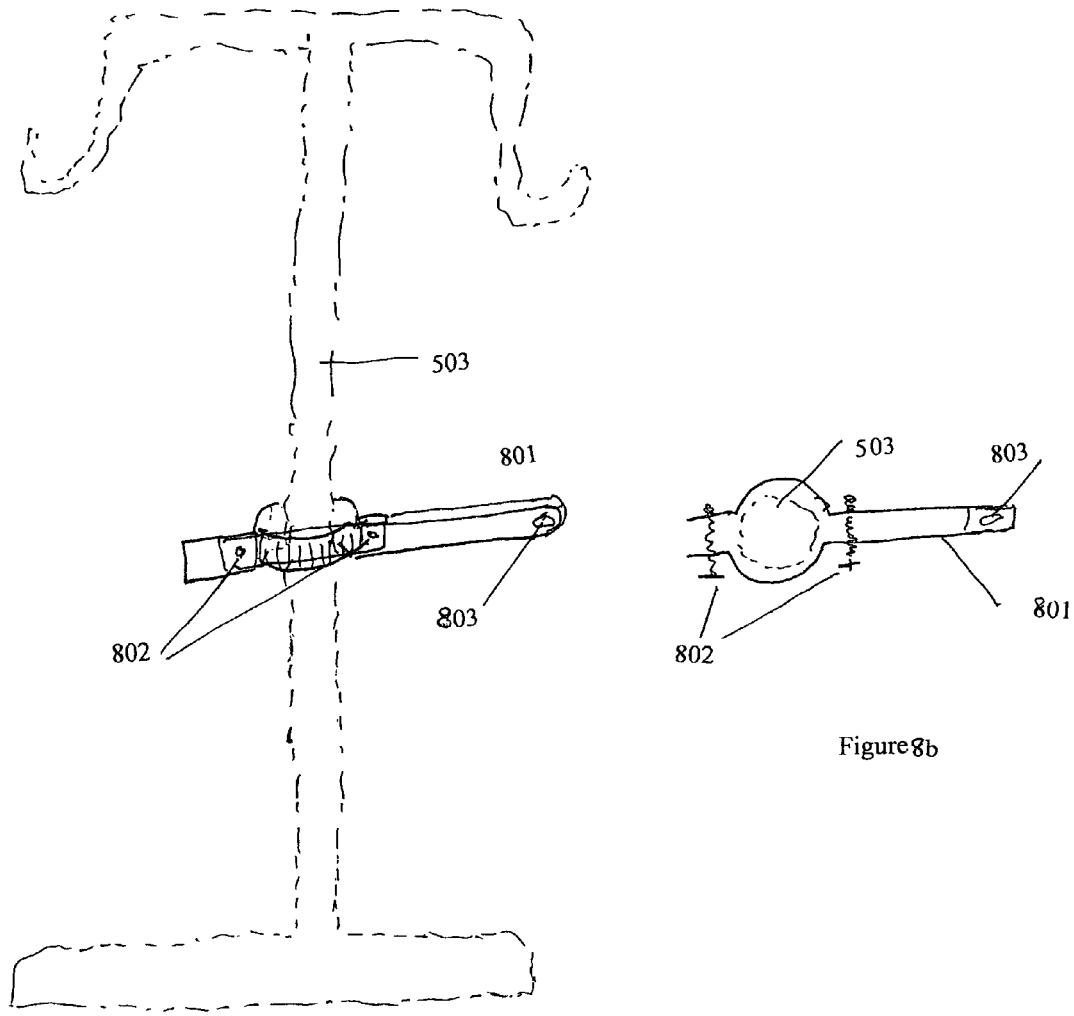
FIG. 8 shows an attachable bracket as part of an installation "kit" for existing i.v. drip line stands.

Additionally, to complete a kit for installation on existing i.v. stands 503, an attachable bracket 801, which provides for anchoring of the end (FIG. 5, 505) of the central line 401 (FIG. 4), may be included. FIG. 8 shows such a generic bracket 801. The bracket 801 attaches to an existing i.v. stand 503 utilizing bolts and nuts through the bolt holes 802 and provides for an eyehole 803. FIG. 8a shows this, with a top-view in FIG. 8b.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention.

It is claimed that:

1. An apparatus for an extensible intravenous drip line, comprising:
a modular helical accordion-like support structure further comprising one or more modules wherein the helical length of the helical accordion-like support structure can be increased by appending one or more modular helical support structure modules;
an intravenous drip line attachable to the helical accordion-like support structure;
an attachment means wherein the intravenous drip line is attached to the helical accordion-like support structure;
a controllable supporting central line disposed interior to loops of the helical accordion-like support structure;
a first end of the controllable supporting central line fixed distally from a controller on a fixed point and a second end of the supporting central line is fixed proximally to a controller wherein the controllable supporting central line acts to suspend the helical accordion-like support structure;
the controllable supporting central line wherein the controllable supporting line may be unwound and rewound from a spring-tensioned roller;
a controller for selectively releasing the spring loaded roller wherein the controllable supporting central line is unwound and rewound; and
each module of the modular helical accordion-like structure disposed wherein at least one end of a first module having an appending means for connecting to a second module.

2. The apparatus of claim 1, further comprising:
the attachment means for the intravenous line including a plurality of continuous arches wherein the arches are integrally molded into the helical accordion-like support structure; and wherein the intravenous drip line tubing is threaded under the arches.

3. The apparatus of claim 2, further comprising arches wherein the arches are not continuous, but separated at their high point into two adjacent sub-arches.

4. The apparatus of claim 1, further comprising:
the attachment means, including glue wherein the intravenous drip line tubing is attached to the intravenous helical accordion-like support structure.

5. The apparatus of claim 1, further comprising:
the attachment means including heat welding wherein a suitable thermoplastic tubing-like-material plastic strip is attached to the center of one side of the helical accordion-like support structure and wherein the intravenous drip line tubing is heat welded to the thermoplastic tubing-like-material plastic strip in the center of one side of the intravenous helical accordion-like support structure.

6. The apparatus of claim 1, further comprising:
the attachment means including tape wherein the intravenous drip line tubing is taped to the intravenous helical accordion-like support structure.

7. The apparatus of claim 1, further comprising:
a wristband attachable to a patient's wrist and a short cord wherein the wristband is attached to the helical accordion-like support structure.

8. The apparatus of claim 1, further comprising an armband attachable to a patient's arm; and a short cord wherein the armband is attached to the helical accordion-like support structure.

9. The apparatus of claim 1, further comprising:
a first helical accordion-like module having a bifurcated substructure on a first end;
a second helical accordion-like module having a bifurcated substructure on a first end;
the bifurcated substructure of the first and second helical accordion-like modules having a flat male blade and a flat female blade;

the flat male blade wherein one or more raised bumps are integrated on a first and a second side of the flat male blade the female blade wherein the female flat blade is further bifurcated into two flat elements;

the female flat bifurcated blade on the first helical accordion-like module is disposed to receive the flat male blade on the second helical accordion-like module;

the female flat bifurcated blade on the second helical accordion-like module is disposed to receive the flat male blade on a first helical accordion-like module; and the female flat bifurcated blade wherein the female flat bifurcated blade has at least one hole disposed to receive at least one bump on the male flat blade.

10. The apparatus of claim 9, further comprising:

an intravenous drip tubing joining element, known in the arts;

the first helical accordion-like support module wherein a first intravenous drip tubing is attached;

the second helical accordion-like support module wherein a second intravenous tubing is attached and wherein the second helical accordion-like module is attached to the first helical accordion-like module by bifurcated substructures of the first and the second helical accordion-like modules; and the bifurcated substructures disposed to accommodate the intravenous drip tubing joining element wherein the intravenous drip tubing joining element joins the first intravenous tubing and the second intravenous tubing.

11. The apparatus of claim 9, further comprising:

an intravenous drip tubing joining element, known in the arts, adapted to receive medicine into intravenous drip lines wherein medicine in a syringe with a hypodermic needle is received;

the first helical accordion-like support module wherein a first intravenous drip tubing is attached;

the second helical accordion-like support module wherein a second intravenous tubing is attached and wherein the second helical accordion-like module is attached to the first helical accordion-like module by bifurcated substructures of the first and the second helical accordion-like modules; and the bifurcated substructures disposed to accommodate the intravenous drip tubing joining element adapted to receive medicine wherein the intravenous drip tubing joining element joins the first intravenous tubing and the second intravenous tubing.

12. The apparatus of claim 1, further comprising a bracket for a kit which is adapted to attach to an intravenous drip line holder wherein the bracket is adapted to anchor the central line.

13. A method for an extensible intravenous drip line, comprising:

supporting an intravenous drip line on a helical accordion-like support structure;

supporting the helical accordion-like structure by a central line disposed to run through the center of the helical accordion-like structure;

changing the effective length of the intravenous drip line by expanding or compressing the helical accordion-like support structure;

preventing the sagging of the helical supporting structure wherein a first end of the central line is disposed to attach to an intravenous drip line stand, and wherein a second end of the central line is disposed to attach to a control element;

controlling the central line with a control element wherein the central line is disposed to wind and unwind on a spring-tensioned roller;

operating the control element by a trigger disposed to allow the central line to unwind on the spring tensioned roller in conjunction with exerting an opening tension on the helical accordion-like support structure; and operating the control element by a trigger disposed to allow the central line to rewind on the spring tensioned roller in conjunction with exerting a closing tension on the helical accordion-like support structure.

14. The method of claim 13, further comprising:

attaching the intravenous drip line tubing to the helical accordion-like support structure by a means including but not limited to gluing, thermoplastic heat welding, taping, and mechanically, by arches on the face of the helical accordion-like support structure.

15. The method of claim 13, further comprising:

appending a first helical accordion-like support structure module to a second helical accordion-like support structure module;

utilizing a bifurcated substructure for appending the first helical accordion-like support structure module to the second helical support structure module;

forming the bifurcated substructure wherein a flat aspect of a first helical accordion-like support structure module is bifurcated into a male flat-like blade and a female flat-like blade;

forming the male flat-like blade wherein the male flat-like blade has one or more raised bumps on a first side and on a second side;

forming the female flat-like blade wherein each flat-like blade comprises two flat elements with space between the two flat elements which is adapted to receive the male blade and wherein the female two flat elements further comprise one or more holes on each of its two flat element disposed to receive the one or more raised bumps on an opposing male blade;

mating a first helical accordion-like support structure having a first bifurcated substructure with a male and a female blade to a second helical accordion-like support structure having a second bifurcated substructure with a female and a male blade wherein the male and female blades of the first bifurcated substructure are disposed to mate with the female and male blades of the second bifurcated substructure, respectively.

16. The apparatus of claim 15, further comprising:

utilizing an intravenous drip tubing joining element, known in the art, wherein the joining element joins two separate intravenous tubes adapting the space between the first bifurcated substructure of the first helical accordion-like support structure module and the second bifurcated substructure of the second helical accordion-like support structure module to accommodate the intravenous drip tubing joining element and joining the intravenous lines, respectively, of at least a first helical accordion-like support structure module and at least a second helical accordion-like support module.

17. The apparatus of claim 16, further comprising:

utilizing an intravenous drip tubing joining element, known in the art, wherein the joining element joins two separate intravenous tubes and wherein the intravenous drip joining tube joining element is a receiving element, known in the arts, disposed to receive medicine into the intravenous drip line by insertion utilizing a hypodermic needle and syringe.

* * * * *